United States Patent
Hatakeyama et al.

(10) Patent No.: US 6,394,613 B1
(45) Date of Patent: May 28, 2002

(54) ANTI-FOGGING AND ANTI-REFLECTION OPTICAL ARTICLE

(75) Inventors: Hideyuki Hatakeyama, Kawasaki; Hideo Ukuda, Yokohama, both of (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/127,606

(22) Filed: Jul. 31, 1998

(30) Foreign Application Priority Data

Aug. 7, 1997 (JP) .............................................. 9-213269

(51) Int. Cl.[7] .............................. G02B 1/00; G02B 1/10; B32B 7/04

(52) U.S. Cl. ........................ 359/507; 359/512; 359/581; 359/582; 428/212; 428/213; 428/336; 428/428; 428/439; 428/441; 428/442; 428/448; 428/451; 428/452; 428/913

(58) Field of Search ................................ 359/507, 512, 359/581, 582; 428/908.8, 457, 450, 432, 212, 213, 336, 439, 441, 442, 448, 451, 452, 913, 215, 216, 312.2, 312.6, 318.4, 319.1, 428

(56) References Cited

U.S. PATENT DOCUMENTS

| | | | | |
|---|---|---|---|---|
| 4,590,117 A | * | 5/1986 | Taniguchi et al. | |
| 4,687,707 A | * | 8/1987 | Matsuo et al. | |
| 4,880,851 A | * | 11/1989 | Yamamoto | |
| 5,194,990 A | * | 3/1993 | Boulos et al. | |
| 5,234,556 A | * | 8/1993 | Oishi et al. | |
| 5,413,865 A | * | 5/1995 | Nakamura et al. | |
| 5,578,377 A | * | 11/1996 | Morimoto et al. | |
| 5,585,186 A | * | 12/1996 | Scholz et al. | |
| 5,594,585 A | * | 1/1997 | Komatsu | 359/512 |
| 5,643,642 A | * | 7/1997 | Oishi et al. | |
| 5,674,625 A | * | 10/1997 | Takahashi et al. | |
| 5,753,373 A | * | 5/1998 | Scholz et al. | |
| 5,854,708 A | * | 12/1998 | Komatsu et al. | 359/507 |
| 5,976,680 A | * | 11/1999 | Ikemori et al. | |
| 6,287,683 B1 | * | 9/2001 | Itoh et al. | |

FOREIGN PATENT DOCUMENTS

| | | | |
|---|---|---|---|
| EP | 0545258 | * | 6/1993 |
| EP | 0 716 051 | | 6/1996 |
| EP | 0 782 015 | | 7/1997 |
| EP | 0 871 046 | | 10/1998 |
| JP | 63-162549 | * | 7/1988 |
| JP | 6-271792 | * | 9/1994 |
| JP | 6-320660 | * | 11/1994 |
| WO | WO 91/08241 | | 6/1991 |
| WO | WO 96/18918 | | 6/1996 |

* cited by examiner

Primary Examiner—Ricky D. Shafer
(74) Attorney, Agent, or Firm—Fitzpatrick, Cella, Harper & Scinto

(57) ABSTRACT

An anti-fogging and anti-reflection optical article included a substrate, a first water-absorbing film provided on the substrate, a thin film of high refractive index provided on the first water-absorbing film, and a second water-absorbing film provided on the thin film of high refractive index. The first water-absorbing film contains a water-absorbing polymer and is provided on the substrate. The thin film of high refractive index includes a polycondensation product of a hydrolysate of a metal alkoxide, and the second water-absorbing film includes a water-absorbing polymer.

10 Claims, 1 Drawing Sheet

ANTI-FOGGING AND ANTI-REFLECTION OPTICAL ARTICLE

BACKGROUND OF THE INVENTION

1. Field of the Invention

The present invention relates to optical articles such as lenses, filters and mirrors, and particularly to optical articles having excellent anti-fogging properties and anti-reflection properties.

2. Related Background Art

In order to prevent fogging of lenses, filters, mirrors and the like, it is common to coat their surfaces with a surfactant. Recently, in place of the surfactant, a water-absorbing substance is also applied to an optical substrate to form a film, thereby preventing fogging.

Water-absorbing substances used to prevent fogging include natural and synthetic polymers. The natural polymers include starch-type polymers, such as hydrolysates of starch-acrylonitrile graft polymers, and cellulosic polymers, such as cellulose-acrylonitrile graft polymers, while the synthetic polymers include polyvinyl-alcohol type polymers, such as crosslinked polyvinyl alcohol, acrylic polymers, such as crosslinked sodium polyacrylate, and polyether-type polymers, such as crosslinked polyethylene glycol diacrylate.

However, the anti-fogging optical articles described in the prior art have the following problems.

1. When a surfactant is used to prevent fogging, the lastingness of its effect is so short that the effect cannot be retained unless the surfactant is applied again after several hours or several days. When soil on the surface of the optical article is wiped out with water or the like, the film of the surfactant comes off, and so its effect is lost.

2. When any of the various water-absorbing substances is applied to form a film for the purpose of preventing fogging, the lastingness of its effect is markedly improved compared with the surfactant. However, when the water-absorbing substance is used as the anti-fogging film, and a layer of a substance having a low refractive index is provided thereon for obtaining an anti-reflection effect, the anti-fogging property tends to be impaired.

3. When the thickness of the water-absorbing substance layer is made thin so as to be odd times a fourth of the objective wavelength whose reflection is to be prevented, to serve itself as an anti-reflection film, the film is often too thin to have sufficient anti-fogging properties.

In order to solve the above-described problems, the present inventors found that when a porous film is used as an anti-reflection film, it is possible to provide an anti-reflection film on the water-absorbing film, retaining the anti-fogging effect of the water-absorbing film. However, such a method has many problems: the anti-fogging properties may vary according to the components of the porous film; absorbed moisture and substances in the moisture may remain both in the porous film and at the interface between the water-absorbing film and the porous film; and when the water-absorbing film swells upon water absorption, the porous film may not follow the swelling and may thus be cracked in some cases.

SUMMARY OF THE INVENTION

It is an object of the present invention to solve the above-described problems and to provide an optical article that have both anti-fogging and anti-reflection properties, thus to provide an optical instrument in which such an optical article is incorporated to prevent dew condensation.

According to the present invention, there is thus provided an anti-fogging and anti-reflection optical article comprising a substrate, a first water-absorbing film provided on the substrate, a thin film of a high refractive index (herein after "highly refractive film") provided on the first water-absorbing film, and a second water-absorbing film provided on the highly refractive film, where the first water-absorbing film comprises a water-absorbing polymer provided on the substrate, the highly refractive film comprises a polycondensation product of a hydrolysate of a metal alkoxide, and the second water-absorbing film comprises a second water-absorbing polymer.

The anti-fogging effect of the anti-fogging and anti-reflection optical article according to the present invention is explained as follows.

Moisture in the air is first absorbed by the second water-absorbing film, which is the outermost layer. The moisture absorbed in the second water-absorbing film passes through the highly refractive film (a film of a high refractive index) which contains, as a main component, the polycondensation product of the hydrolyzate of the metal alkoxide, and is absorbed by the first water-absorbing film. When the moisture absorbed in the first water-absorbing film is released to the outside in the reverse route, that is, it passes through the highly refractive film, is absorbed by the second water-absorbing film and is finally released into the air. Such a process can prevent the moisture and substances in the moisture from remaining in the highly refractive film and at the interface between the refractive film and the first or second water-absorbing film. Therefore, failure, such as staining of optical articles caused by the remaining moisture, is prevented.

At the same time, the highly refractive film can also play a role to adhere the first water-absorbing film to the second water-absorbing film. Since this film has higher flexibility compared with general inorganic thin films, it can follow swelling of the water-absorbing films upon water absorption, and so the highly refractive film would not crack by swelling of the water-absorbing films.

DETAILED DESCRIPTION OF THE PREFERRED EMBODIMENTS

Figure 1:
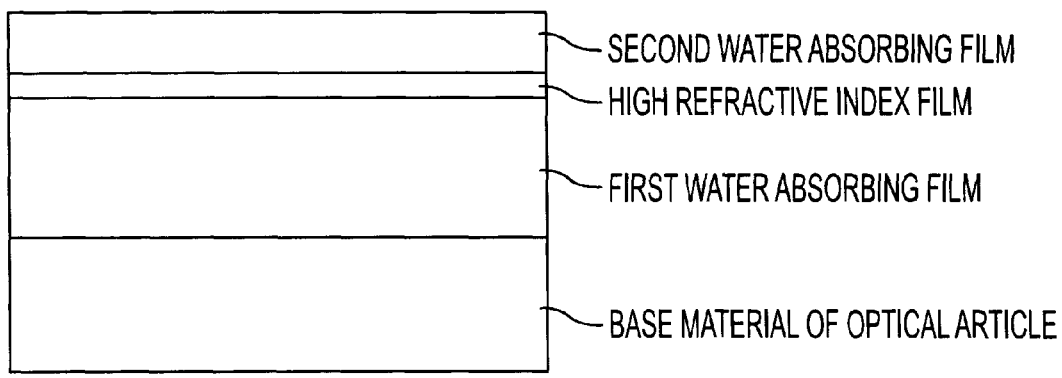
FIG. 1 shows a partial sectional schematic view of the anti-fogging and anti-reflection optical article of the present invention.

Examples of water-absorbing polymers forming the water-absorbing film include semi-natural polymers including starch-type polymers, such as hydrolysates of starch-acrylonitrile graft polymers, and cellulosic polymers, such as cellulose-acrylonitrile graft polymers; and synthetic polymers including polyvinyl-alcohol-type polymers, such as crosslinked polyvinyl alcohol, acrylic polymers, such as crosslinked sodium polyacrylate, and polyether-type polymers, such as crosslinked polyethylene glycol diacrylate. Of these, the high water-absorbent substances, such as polyacrylics and polyvinyl alcohol, are preferably used.

Examples of the polyacrylics include polyacrylic acid, polymethacrylic acid, polyacrylamide and salts (potassium polyacrylate, sodium polyacrylate, etc.) thereof. Polyacrylic acid and polymethacrylic acid are preferably used.

The number average molecular weights of the polyacrylics are preferably within a range of from 3,000 to 1,500,000, particularly from 50,000 to 750,000.

Both or one of the first and second water-absorbing films each comprised of a water-absorbing polymer can be formed by conducting a polycondensation reaction of a hydrolysate of a metal alkoxide in the presence of a water-absorbing polymer, thereby obtaining a water-absorbing film further improved in water absorption performance. Preferable examples of such a metal alkoxide include compounds represented by formulae

and

wherein M is an atom selected from the group consisting of Si, Al, Ti, Zr, Ca, Fe, V, Sn, Li, Be, B and P, R is an alkyl, X is an alkyl, alkyl having a functional group, or halogen, a is a valence of M, and n is an integer of from 1 to a.

As X in the above formula (II), carbonyl, carboxyl, amino, vinyl, or alkyl having an epoxy is preferred.

Particularly preferable examples of the metal alkoxides include $Si(OC_2H_5)_4$, $Al(O\text{-iso-}C_3H_7)_3$, $Ti(O\text{-iso-}C_3H_7)_4$, $Zr(O\text{-t-}C_4H_9)_4$, $Zr(O\text{-n-}C_4H_9)_4$, $Ca(OC_2H_5)_2$, $Fe(OC_2H_5)_3$, $V(O\text{-iso-}C_3H_7)_4$, $Sn(O\text{-t-}C_4H_9)_4$, $Li(OC_2H_5)$, $Be(OC_2H_5)_2$, $B(OC_2H_5)_3$, $P(OC_2H_5)_2$ and $P(OCH_3)_3$.

The water-absorbing film formed by conducting a polycondensation reaction of a hydrolysate of the metal alkoxide in the presence of a water-absorbing polymer can be produced by preparing a reaction solution containing: at least one of a metal alkoxide, a hydrolysate of the metal alkoxide and a low molecular-weight polycondensation product of the hydrolysate; a water-absorbing polymer; and a catalyst for accelerating the polycondensation reaction of the hydrolysate, applying the reaction solution to the surface of a substrate, and then heat-treating the applied film. The term "containing at least one of a metal alkoxide, a hydrolysate of the metal alkoxide and a low molecular weight polycondensation product of the hydrolysate" refers to one of the following four cases.

(1) A metal alkoxide is used for the preparation of the reaction solution, and the hydrolyzing reaction thereof is caused after the preparation of the reaction solution.

(2) A hydrolysate of the metal alkoxide obtained by conducting the hydrolyzing reaction of a metal alkoxide is used for the preparation of the reaction solution.

(3) A low molecular-weight polycondensation product, obtained by partially polycondensing the hydrolysate of a metal alkoxide, is used for the preparation of the reaction solution.

(4) At least two of a metal alkoxide, the hydrolysate thereof and the low molecular-weight polycondensation product of the hydrolysate are used for the preparation of the reaction solution.

When a metal alkoxide is contained in the reaction solution prepared, the hydrolysis of the metal alkoxide and the polycondensation of the hydrolysate thereof are carried out in the presence of the water-absorbing polymer. With the progress of the polycondensation reaction in the reaction solution, the viscosity of the solution increases. Therefore, the application of the reaction solution to the substrate is conducted before the viscosity becomes too high.

The solution containing the water-absorbing polymer to form the water-absorbing film can be applied by such a method as dip coating, spray coating and spin coating. It is also effective to accelerate a cross-linking reaction between the water-absorbing polymer and the polycondensation product by heating or ultraviolet-light irradiation after coating.

The thickness of the first water-absorbing film is desirably within a range of from 1 to 20 μm. When the thickness of the water-absorbing film is smaller than 1 μm, a sufficient anti-fogging effect cannot be obtained. If the thickness is greater than 20 μm, it is difficult to obtain a uniform water-absorbing film.

The highly refractive film formed as an outer layer of the first water-absorbing film contains a polycondensation product of a hydrolysate of a metal alkoxide. As a preferable metal alkoxide, there may be used the compounds represented by the above formulae (I) or (II). As the particularly preferable metal alkoxide, included are aluminum alkoxides such as $Al(OC_2H_5)_3$ and $Al(OCH(CH_3)_2)_3$, titanium alkoxides such as $Ti(OC_2H_5)_4$ and $Ti(OCH(CH_3)_2)_4$, zirconium alkoxides such as $Zr(OC_2H_5)_4$ and $Zr(OCH(CH_3)_2)_4$, $Ca(OC_2H_5)_2$, $Fe(OC_2H_5)_3$, $V(O\text{-iso-}C_3H_7)_4$, $Sn(O\text{-t-}C_4H_9)_4$, $Li(OC_2H_5)$, $Be(OC_2H_5)_2$, $B(OC_2H_5)_3$, $P(OC_2H_5)_2$ and $P(OCH_3)_3$.

The highly refractive film can be formed by applying a solution containing at least one of a metal alkoxide, a hydrolysate of the metal alkoxide, and a low molecular weight polycondensation product of the hydrolysate to the surface of the first water-absorbing film.

The refractive index ($n_1$) of the highly refractive film mainly composed of a metal alkoxide is preferably higher than those of the first and second water-absorbing films. Particularly, it is desirably at least 1.7.

The optical thickness ($n_1d_1$) of the highly refractive film is preferably 300 nm or less, so that migration of water through the thin film to the first or second water-absorbing film can easily occur. Besides, it is preferred from the viewpoint of achieving a good anti-reflection effect that the optical thickness ($n_1d_1$) of the highly refractive film should be preset so as to satisfy a formula $$0.8 \times k\lambda_1/2 \leq n_1d_1 \leq 1.2 \times k\lambda_1/2 \tag{3}$$

or $$0.8 \times k\lambda_1/4 \leq n_1d_1 \leq 1.2 \times k\lambda_1/4 \tag{4}$$

wherein k is a positive odd number, $n_1$ is a refractive index of the highly refractive film, $d_1$ is a thickness of the highly refractive film, and $\lambda_1$ is a design wavelength selected from the range of from 400 to 900 nm.

Moreover, it is preferred from the viewpoint of achieving a good anti-reflection effect that the optical thickness ($n_2d_2$) of the second water-absorbing film should be preset so as to satisfy a formula $$0.8 \times k\lambda_2/4 \leq n_2d_2 \leq 1.2 \times k\lambda_2/4 \tag{5}$$

wherein k is a positive odd number, $n_2$ is a refractive index of the second water-absorbing film, $d_2$ is a thickness of the second water-absorbing film, and $\lambda_2$ is a design wavelength selected from the range of from 400 to 900 nm.

In order to control the refractive index (n), inorganic fine particles of an oxide of a metal selected from the group consisting of Ti, Ce, Zr, Sn, Sb, Ta and Si, or of a metal fluoride, such as $MgF_2$, may be added to the first and second water-absorbing films and the highly-refractive film, as needed, as shown in FIG. 1.

The present invention will hereinafter be described more specifically by the following examples. However, the present invention is not limited to these examples.

EXAMPLE 1

To 986.4 g of Liquid A were added 13.6 g of Liquid B. Liquid A was prepared by adding 80 parts by weight of methanol to 2 parts by weight of a 25% aqueous solution of polyacrylic acid having a number average molecular weight of 300,000, and liquid B was prepared by adding 3 g of tetraethoxysilane (trade name: Ethylsilicate 40, product of Colcoat Co., Ltd.), 4.6 g of a silane coupling agent (trade name: SH6040, product of Toray Dow Corning Silicone Co., Ltd.), 0.1 g of 2N hydrochloric acid and 0.1 g of N,N-dimethylbenzylamine to a solution prepared by dissolving 0.5 g of aluminum isopropoxide, 0.4 g of 35% hydrochloric acid and 0.9 g of water in 4 g of ethanol. The mixture was stirred for 2 minutes at ordinary temperature to prepare Coating Formulation C.

A glass (BK7) substrate having a thickness of 1.2 mm was dipped in the thus-prepared Coating Formulation C and lifted at a rate of 80 mm/min, thereby coating the substrate. The coated substrate was then heated and dried at 150° C. for 10 minutes to form a first water-absorbing film. The formed water-absorbing film was transparent and had a film thickness of about 7 µm, and its refractive index was 1.48.

Coating Formulation D for the highly refractive film was then prepared by dissolving 20 g of titanium tetraisopropoxide into 80 g of isobutyl acetate.

The glass substrate, on which the water-absorbing film had been formed, was dipped in Coating Formulation D and lifted at a rate of 80 mm/min, thereby coating the water-absorbing film. The thus-treated substrate was then heated and dried at 150° C. for 15 minutes to form a highly refractive film. The thus-formed highly refractive index film had an optical thickness of 30 nm (optical thickness=n (refractive index)×d (thickness) of the film) and a refractive index of 1.75.

In 80 g of a mixed solvent of water and methanol (mixing ratio of water to methanol=1:1), were dissolved 20 g of the above-prepared Coating Formulation C, thereby preparing Coating Formulation E.

The glass substrate, on which the water-absorbing film and highly-refractive index film had been formed in that order, was dipped in Coating Formulation E and lifted at a rate of 80 mm/min, thereby coating the highly-refractive index film. The thus-treated substrate was then heated and dried at 150° C. for 15 minutes to form a second water-absorbing film. At this time, the optical thickness (n (refractive index)×d (thickness) of the film) of the second water-absorbing film was controlled to 135 nm. The second water-absorbing film had a refractive index of 1.48.

The thus-obtained optical article sample was subjected to the following four performance tests.
1. Anti-reflection properties:

The light transmittance of a sample was measured at 550 nm. (Rank A: the transmittance is at least 96%, Rank B: the transmittance is lower than 96%.)
2. Anti-fogging properties:

A sample was moved from an environment of 5° C. into an environment of 30° C. and 80% RH to observe the occurrence of fogging. (Rank A: no fogging occurred, Rank C: fogging occurred.)
3. Staining on film:

A sample was left to stand for 1 minute in water to observe the occurrence of staining on film. (Rank A: no staining on film occurred, Rank B: staining on film occurred.)
4. Breakdown of film upon water absorption:

A sample was left to stand for 200 hours in an environment of 60° C. and 90% RH to observe the occurrence of breakdown of film. (Rank A: no breakdown of film occurred, Rank D: breakdown of film occurred.)

The results of the tests are shown in Table 1. As shown in Table 1, an anti-fogging and anti-reflection optical article satisfying all the performance characteristics tested was obtained.

COMPARATIVE EXAMPLE 1

A glass (trade name: S-LAL12, product of Ohara Co.) substrate having a thickness of 1.2 mm was dipped in Coating Formulation C used in Example 1 and lifted at a rate of 5 mm/min, thereby coating the substrate. The coated substrate was then heated and dried at 150° C. for 10 minutes to form a water-absorbing film. The optical thickness (the product of refractive index, n and thickness, d of the water-absorbing film) of the water-absorbing film was controlled to 135 nm. In this case, the refractive indices of the substrate (S-LAL12) and the water-absorbing film were 1.68 and 1.48, respectively. In comparison with Example 1, only one film corresponding to the second water-absorbing film in Example 1 was formed on the substrate. The thus-obtained optical-article sample was subjected to the same tests as in Example 1. The results are shown in Table 1.

As shown in Table 1, the optical article sample satisfied the predetermined performance as to the anti-reflection property, staining on film and breakdown of film upon water absorption, but underwent fogging in the test of anti-fogging properties.

COMPARATIVE EXAMPLE 2

A glass (BK7) substrate having a thickness of 1.2 mm was dipped in Coating Formulation C used in Example 1 and lifted at a rate of 80 mm/min, thereby coating the substrate. The coated substrate was then heated and dried at 150° C. for 10 minutes to form a first water-absorbing film. The thus-formed water-absorbing film was transparent and had a film thickness of about 7 µm, and its refractive index was 1.48.

A $ZrO_2$ film was formed on the first water-absorbing film by a vacuum deposition process so as to give an optical thickness of 30 nm. The vacuum deposition of the $ZrO_2$ film was conducted under conditions of a degree of vacuum of $4 \times 10^{-4}$ Torr in an atmosphere of argon. The $ZrO_2$ film had a refractive index of 1.74 and was a porous film of a packing rate of 70%.

In 80 g of a mixed solvent of water and methanol (mixing ratio of water to methanol=1:1), were dissolved 20 g of the above Coating Formulation C, thereby preparing Coating Formulation E.

The glass substrate, on which the first water-absorbing film and $ZrO_2$ film had been formed in that order, was dipped in Coating Formulation E and lifted at a rate of 80 mm/min, thereby coating the $ZrO_2$ film. The thus-treated substrate was then heated and dried at 150° C. for 15 minutes to form a second water-absorbing film. At this time, the optical thickness (the product of refractive index, n and thickness, d of the water-absorbing film) of the second water-absorbing film was controlled to 135 nm. The second water-absorbing film had a refractive index of 1.48.

The thus-obtained optical article sample was subjected to the same tests as in Example 1. The results are shown in Table 1. As a result, the article sample satisfied the predetermined performance as to the anti-reflection property, anti-fogging property and staining on film. However, the porous, highly refractive film composed of $ZrO_2$ did not follow the swelling of the water-absorbing films upon water absorption, so that the $ZrO_2$ film cracked, and the sample became unsuitable as an optical article.

TABLE 1

|  | Ex. 1 | Comp. Ex. 1 | Comp. Ex. 2 |
|---|---|---|---|
| Anti-reflection properties | A | A | A |
| Anti-fogging properties | A | C | A |
| Staining on film | A | — | A |
| Breakdown of film upon water absorption | A | — | D (Breakdown of $ZrO_2$) |

EXAMPLE 2

Several experiments were carried out in the same manner as in Example 1 except that the thickness of the first water-absorbing film was varied.

Glass (BK7) substrates each having a thickness of 1.2 mm were dipped in Coating Formulation C used in Example 1 and lifted while controlling their lifting rates in such a manner that the film thickness of a first water-absorbing film was 0.5 μm for Experimental Example 2, 1 μm for Experimental Example 3, 7 μm for Experimental Example 4, 20 μm for Experimental Example 5 and 25 μm for Experimental Example 6, thereby coating the substrates. The coated substrates were then heated and dried at 150° C. for 10 minutes to form the respective first water-absorbing films.

In 80 g of isobutyl acetate, were dissolved 20 g of titanium tetraisopropoxide, thereby preparing Coating Formulation D for highly refractive film.

Each of the glass substrates, on which the water-absorbing film had been formed, was dipped in Coating Formulation D and lifted at a rate of 200 mm/min, thereby coating the water-absorbing film. The thus-treated substrate was then heated and dried at 150° C. for 15 minutes to form a highly refractive film. The thus-formed highly refractive film had an optical thickness (the product of refractive index, n and thickness, d of the film) of 135 nm and a refractive index of 1.75.

In 80 g of a mixed solvent of water and methanol (mixing ratio of water to methanol=1:1), were dissolved 20 g of the above Coating Formulation C, thereby preparing Coating Formulation E.

Each glass substrate, on which the water-absorbing film and highly refractive film had been formed in that order, was dipped in Coating Formulation E and lifted at a rate of 80 mm/min, thereby coating the highly-refractive index film. Thus-treated each substrate was then heated and dried at 150° C. for 15 minutes to form a second water-absorbing film. At this time, the optical thickness (the product of refractive index, n and thickness, d of the film) of the second water-absorbing film was controlled to 135 nm. The second water-absorbing film had a refractive index of 1.48.

The thus-obtained optical article samples of Experimental Examples 2 to 6 were subjected to the following two performance tests.

1. Anti-fogging properties:

A sample was moved from an environment of 5° C. into an environment of 30° C. and 80% RH to observe whether fogging occurred or not. (Rank A: no fogging occurred, Rank B: fogging occurred right after moving, but vanished within 2 seconds.)

2. Deformation of film upon water absorption:

A sample was left to stand for 1 minute in water to observe whether some film showed deformation or not (Rank A: change in transmittance before and after the immersion in water was at most 2%, Rank B: change in transmittance was at most 4%.)

The results of the tests are shown in Table 2.

TABLE 2

|  | Thickness of first water-absorbing film (μm) | Anti-fogging properties | Deformation of film upon water absorption |
|---|---|---|---|
| Exp. Ex. 2 | 0.5 | B | A |
| Exp. Ex. 3 | 1 | A | A |
| Exp. Ex. 4 | 7 | A | A |
| Exp. Ex. 5 | 20 | A | A |
| Exp. Ex. 6 | 25 | A | B |

EXAMPLE 3

Several experiments were carried out in the same manner as in Example 1, except that the thickness of the second water-absorbing film in Example 1 was varied.

Glass (BK7) substrates each having a thickness of 1.2 mm were dipped in Coating Formulation C used in Example 1 and lifted at a rate of 80 mm/min, thereby coating the substrates. The coated substrates were then heated and dried at 150° C. for 10 minutes to form the first water-absorbing film. The thus-formed water-absorbing films were transparent and each had a film thickness of about 7 μm, and their refractive indices were 1.48.

In 80 g of isobutyl acetate, were dissolved 20 g of titanium tetraisopropoxide, thereby preparing Coating Formulation D for highly-refractive film.

The glass substrates, on which the water-absorbing film had been formed, were dipped in Coating Formulation D and lifted at a rate of 200 mm/min, thereby coating the water-absorbing films. The thus-treated substrates were then heated and dried at 150° C. for 15 minutes to form a highly-refractive film. The thus-formed highly-refractive index films each had an optical thickness (the product of refractive index, n and thickness, d of the film) of 135 nm and a refractive index of 1.75.

In 80 g of a mixed solvent of water and methanol (mixing ratio of water to methanol=1:1), were dissolved 20 g of the above Coating Formulation C, thereby preparing Coating Formulation E.

The glass substrates, on which the water-absorbing film and highly-refractive index film had been formed in that order, were dipped in Coating Formulation E and lifted while controlling their lifting rates in such a manner that the optical thickness (the product of refractive index, n and thickness, d of the film) of each second water-absorbing film was 100 nm for Experimental Example 7, 110 nm for Experimental Example 8, 135 nm for Experimental Example 9, 160 nm for Experimental Example 10 and 180 nm for Experimental Example 11, thereby coating the highly-refractive film. The thus-treated substrates were then heated and dried at 150° C. for 15 minutes to form the second water-absorbing films. At this time, the refractive indices of the second water-absorbing films were each 1.48.

The transmittances of the thus-obtained optical article samples of Experimental Examples 7 to 11 were measured to determine the wavelength at which the maximum transmittance was obtained. In this case, the design wavelength was 550 nm.

As a result, the wavelength at which the maximum values of transmittance was obtained was 400 nm (Experimental Example 7), 440 nm (Experimental Example 8), 540 nm (Experimental Example 9), 640 nm (Experimental Example 10) and 720 nm (Experimental Example 11). In Experimental Examples 7, 8 and 11, a deviation from the design wavelength exceeds 100 nm but they are all at the usable level(see Table 3).

TABLE 3

|  | Refractive index n of second water-absorbing film | Thickness d of second water-absorbing film (nm) | Optical thickness nd of second water-absorbing film | Compatibility with design wavelength |
|---|---|---|---|---|
| Exp. Ex. 7 | 1.48 | 70 | 100 | B |
| Exp. Ex. 8 | 1.48 | 75 | 110 | B |
| Exp. Ex. 9 | 1.48 | 90 | 135 | A |
| Exp. Ex. 10 | 1.48 | 110 | 160 | AB |
| Exp. Ex. 11 | 1.48 | 120 | 180 | B |

Compatibility with the design wavelength:
Rank A: a fully sufficient level from the viewpoint of performance
Rank B: a usable level
Rank AB: an intermediate level between A and B.

EXAMPLE 4

Experiments were carried out in the same manner as in Example 1, except that the thickness of the highly refractive film in Example 1 was varied.

Glass (BK7) substrates, each having a thickness of 1.2 mm, were dipped in Coating Formulation C used in Example 1 and lifted at a rate of 80 mm/min, thereby coating the substrates. The coated substrates were then heated and dried at 150° C. for 10 minutes to form the first water-absorbing film. The thus-formed water-absorbing films were transparent and each had a film thickness of about 7 μm, and their refractive indices were 1.48.

In 80 g of isobutyl acetate, were dissolved 20 g of titanium tetraisopropoxide, thereby preparing Coating Formulation D for highly-refractive index film.

The glass substrates, on which the water-absorbing film had been formed, were dipped in Coating Formulation D and lifted while controlling their lifting rates in such a manner that the optical thickness (the product of refractive index, n and thickness, d of the film) of the resulting highly refractive film after drying was 270 nm for Experimental Example 12 and 540 nm for Experimental Example 13, thereby coating the respective water-absorbing films. The thus-treated substrates were then heated and dried at 150° C. for 15 minutes. The thus-formed highly refractive films each had a refractive index of 1.75.

In 80 g of a mixed solvent of water and methanol (mixing ratio of water to methanol=1:1), were dissolved 20 g of the above Coating Formulation C, thereby preparing Coating Formulation E.

The glass substrates, on which the water-absorbing film and highly-refractive index film had been formed in that order, were dipped in Coating Formulation E and lifted at a rate of 80 mm/min, thereby coating the respective highly refractive films. The thus-treated substrates were then heated and dried at 150° C. for 15 minutes to form the second water-absorbing films.

The anti-reflection properties and anti-fogging properties of the thus-obtained optical article samples of Experimental Examples 12 and 13 are shown in Table 4.

TABLE 4

|  | Optical thickness of titanium isopropoxide | Anti-reflection properties | Anti-fogging properties |
|---|---|---|---|
| Exp. Ex. 12 | 270 nm | A | A |
| Exp. Ex. 13 | 540 nm | A | B |

EXAMPLE 5

Optical article samples were prepared in the same manner as in Example 1 except that zirconium tetraisopropoxide (Experimental Example 14), aluminum triisopropoxide (Experimental Example 15) and tin tetra-t-butoxide (Experimental Example 16) were used in place of titanium tetraisopropoxide in Example 1.

In Experimental Example 14, Coating Formulation F for highly refractive film prepared by dissolving 20 g of zirconium tetraisopropoxide in 80 g of isobutyl acetate was used. The highly-refractive index film formed had an optical thickness of about 50 nm and a refractive index of 1.95.

In Experimental Example 15, Coating Formulation G for highly refractive film prepared by dissolving 20 g of aluminum triisopropoxide in 80 g of isobutyl acetate was used. The highly refractive film formed had an optical thickness of about 40 nm and a refractive index of 1.65. In Experimental Example 16, Coating Formulation H for highly-refractive index film, prepared by dissolving 20 g of tin tetra-t-butoxide in 80 g of isobutyl acetate, was used. The highly refractive film formed had an optical thickness of about 30 nm and a refractive index of 1.62.

These optical-article samples thus obtained were subjected to all the tests described in Example 1. As a result, it was confirmed that they had the same performance as that obtained in Example 1.

EXAMPLE 6

The anti-fogging and anti-reflection optical article obtained in Example 1 was set as binocular eyepieces. The binoculars were moved from a room of −5° C. into a room of 30° C. and 80% RH to check the performance of the binoculars at that point. As a result, there was no inconvenience upon observation due to fogging of eyepieces, which is observed in ordinary binoculars.

EXAMPLE 7

To 900 g of a liquid obtained by adding 80 parts by weight of methanol to 2 parts by weight of a 25% aqueous solution of polyacrylic acid having a number average molecular weight of 300,000, were added 700 g of a liquid obtained by adding 80 parts by weight of methanol to 2 parts by weight of a 10% aqueous solution of polyvinyl alcohol having a saponification degree of 82 mol %. The mixture was stirred for 30 minutes at ordinary temperature to prepare Coating Formulation I.

A glass (BK7) substrate having a thickness of 1.2 mm was dipped in the thus-prepared Coating Formulation I and lifted at a rate of 80 mm/min, thereby coating the substrate. The coated substrate was then heated and dried at 150° C. for 30 minutes to form a first water-absorbing film. The thus-formed water-absorbing film was transparent and had a film thickness of about 5 μm, and its refractive index was 1.47.

In 80 g of isobutyl acetate, were dissolved 20 g of titanium tetraisopropoxide, thereby preparing Coating Formulation D for highly refractive film.

The glass substrate, on which the water-absorbing film had been formed, was dipped in Coating Formulation D and lifted at a rate of 80 mm/min, thereby coating the water-absorbing film. The thus-treated substrate was then heated and dried at 150° C. for 15 minutes to form a highly refractive film. The thus-formed highly refractive film had an optical thickness of 30 nm and a refractive index of 1.75.

In 80 g of a mixed solvent of water and methanol (mixing ratio of water to methanol=1:1), were dissolved 20 g of the above-prepared Coating Formulation I, thereby preparing Coating Formulation J.

The glass substrate, on which the water-absorbing film and highly-refractive index film had been formed in that order, was dipped in Coating Formulation J and lifted at a rate of 120 mm/min, thereby coating the highly-refractive index film. The thus-treated substrate was then heated and dried at 150° C. for 30 minutes to form a second water-absorbing film. The optical thickness of the second water-absorbing film was 135 nm, and its refractive index was 1.47.

The thus-obtained anti-fogging and anti-reflection optical article was evaluated in the same manner as in Example 1. As a result, similar results were obtained, but its mechanical strength was somewhat poor.

What is claimed is:

1. An anti-fogging and anti-reflection optical article comprising a substrate, a first water-absorbing film provided on the substrate, a thin film of high refractive index provided on the first water-absorbing film having a thickness of from 1 to 20 µm, and a second water-absorbing film provided on the thin film of high refractive index, the first water-absorbing film containing a water-absorbing polymer and provided on the substrate, the thin film of high refractive index comprising a polycondensation product of a hydrolysate of a metal alkoxide, and the second water-absorbing film containing a second water-absorbing polymer.

2. The anti-fogging and anti-reflection optical article according to claim 1, wherein at least one of the first water-absorbing film and the second water-absorbing film is formed by conducting a polycondensation reaction of a hydrolysate of a metal alkoxide in the presence of the water-absorbing polymer.

3. The anti-fogging and anti-reflection optical article according to claim 1, wherein the water-absorbing polymer contained in at least one of the first water-absorbing film and the second water-absorbing film is polyacrylic acid.

4. The anti-fogging and anti-reflection optical article according to claim 1, wherein the refractive index of the thin film of high refractive index is higher than those of the first and second water absorbing films.

5. The anti-fogging and anti-reflection optical article according to claim 1, wherein the metal alkoxide is a compound represented by a formula $$M(OR)_a \qquad (I)$$

or $$(OR)_n(X)_{a-n} \qquad (II)$$

wherein M is an atom selected from the group consisting of Si, Al, Ti, Zr, Ca, Fe, V, Sn, Li, Be, B and P, R is an alkyl radical, X is an alkyl radical, an alkyl radical having a functional group, or halogen, a is a valence of M, and n is an integer of from 1 to a.

6. The anti-fogging and anti-reflection optical article according to claim 1, wherein the metal alkoxide is a compound selected from the group consisting of $Si(OC_2H_5)_4$, $Al(O\text{-iso-}C_3H_7)_3$, $Ti(O\text{-iso-}C_3H_7)_4$, $Zr(O\text{-t-}C_4H_9)_4$, $Zr(O\text{-n-}C_4H_9)_4$, $Ca(OC_2H_5)_2$, $Fe(OC_2H_5)_3$, $V(O\text{-iso-}C_3H_7)_4$, $Sn(O\text{-t-}C_4H_9)_4$, $Li(OC_2H_5)$, $Be(OC_2H_5)_2$, $B(OC_2H_5)_3$, $P(OC_2H_5)_2$ and $P(OCH_3)_3$.

7. The anti-fogging and anti-reflection optical article according to claim 1, wherein the optical thickness $n_1d_1$ of the high refractive film is at most 300 nm.

8. The anti-fogging and anti-reflection optical article according to claim 1, wherein the first water-absorbing film, the thin film of high refractive index and the second water-absorbing film are formed on the substrate selected from the group consisting of lenses, filters and mirrors.

9. An anti-fogging and anti-reflection optical article comprising a substrate, a first water-absorbing film provided on the substrate, a thin film of high refractive index provided on the first water absorbing film, and a second water-absorbing film provided on the thin film of high refractive index, the first water-absorbing film containing a water-absorbing polymer and provided on the substrate, the thin film of high refractive index comprising a polycondensation product of a hydrolysate of a metal alkoxide, and the second water-absorbing film containing a second water-absorbing polymer, and the water-absorbing polymer contained in at least one of the first water-absorbing film and the second water-absorbing film being polyacrylic acid.

10. An anti-fogging and anti-reflection optical article comprising a substrate, a first water-absorbing film providing on the substrate, a thin film of high refractive index provided on the first water-absorbing film, and a second water-absorbing film provided on the thin film of high refractive index, the first water-absorbing film containing a water-absorbing polymer and provided on the substrate, the thin film of high refractive index comprising a polycondensation product of a hydrolysate of a metal alkoxide, and the second water-absorbing film containing a second water-absorbing polymer, and the metal alkoxide being a compound selected from the group consisting of $Si(OC_2H_5)_4$, $Al(O\text{-iso-}C_3H_7)_3$, $Ti(O\text{-iso-}C_3H_7)_4$, $Zr(O\text{-t-}C_4H_9)_4$, $Zr(O\text{-n-}C_4H_9)_4$, $Ca(OC_2H_5)_2$, $Fe(OC_2H_5)_3$, $V(O\text{-iso-}C_3H_7)_4$, $Sn(O\text{-t-}C_4H_9)_4$, $Li(OC_2H_5)$, $Be(OC_2H_5)_2$, $B(OC_2H_5)_3$, $P(OC_2H_5)_2$ and $P(OCH_3)_3$.

* * * * *

UNITED STATES PATENT AND TRADEMARK OFFICE
CERTIFICATE OF CORRECTION

PATENT NO.    : 6,394,613 B1
DATED         : May 28, 2002
INVENTOR(S)   : Hatakeyama et al.

It is certified that error appears in the above-identified patent and that said Letters Patent is hereby corrected as shown below:

<u>Column 11,</u>
Line 50, "water absorbing" should read -- water-absorbing --.

<u>Column 12,</u>
Line 28, "water absorbing" should read -- water-absorbing --.
Line 40, "ing on" should read -- ed on --.

Signed and Sealed this

Fourteenth Day of January, 2003

JAMES E. ROGAN
*Director of the United States Patent and Trademark Office*